(12) United States Patent
Tsuchida et al.

(10) Patent No.: US 7,569,235 B2
(45) Date of Patent: Aug. 4, 2009

(54) COMPOSITIONS FOR TREATING AND/OR PREVENTING POLLINOSIS

(75) Inventors: Yuuzou Tsuchida, Tokyo (JP); Kotarou Tsuchida, Tokyo (JP); Kenjirou Tsuchida, Tokyo (JP)

(73) Assignee: Hououdou Co., Ltd., Tokyo (JP)

( * ) Notice: Subject to any disclaimer, the term of this patent is extended or adjusted under 35 U.S.C. 154(b) by 181 days.

(21) Appl. No.: 11/484,679

(22) Filed: Jul. 12, 2006

(65) Prior Publication Data

US 2006/0251752 A1  Nov. 9, 2006

Related U.S. Application Data

(63) Continuation of application No. 10/949,367, filed on Sep. 27, 2007, now abandoned, which is a continuation of application No. PCT/JP03/03822, filed on Mar. 27, 2003.

(30) Foreign Application Priority Data

Mar. 27, 2002  (JP)  ................................ 2002-88823

(51) Int. Cl.
    *A61K 36/00*  (2006.01)
(52) U.S. Cl. ..................................... 424/725
(58) Field of Classification Search ........................ None
    See application file for complete search history.

(56) References Cited

U.S. PATENT DOCUMENTS

| 5,494,667 | A | 2/1996 | Uchida et al. |
| 5,939,076 | A * | 8/1999 | Allocca ....................... 424/400 |
| 6,187,324 | B1 | 2/2001 | Ogi et al. |
| 7,211,567 | B1 * | 5/2007 | Kotani et al. .................. 514/25 |
| 2003/0113387 | A1 | 6/2003 | Tsuchida et al. |
| 2005/0244515 | A1 | 11/2005 | Tsuchida et al. |
| 2006/0029627 | A1 | 2/2006 | Tsuchida et al. |
| 2006/0029689 | A1 | 2/2006 | Tsuchida et al. |
| 2006/0127330 | A1 | 6/2006 | Tsuchida et al. |
| 2006/0177525 | A1 * | 8/2006 | Takagaki et al. ............. 424/725 |

FOREIGN PATENT DOCUMENTS

| EP | 1172109 A9 | 1/2001 |
| JP | 9-278662 | 10/1997 |
| JP | 9-278662 A | 10/1997 |
| JP | 2000-69946 A | 3/2000 |
| JP | 2001-64192 A | 3/2001 |
| JP | 2001064159 * | 3/2001 |
| JP | 2001-114686 A | 4/2001 |
| JP | 2001-258486 | 9/2001 |
| WO | 00/57888 A1 | 10/2000 |

OTHER PUBLICATIONS www.pfaf.org/database/plants.php?Sasa+veitchii—accessed Aug. 2008.*
U.S. Appl. No. 11/484,679, filed Jul. 12, 2006, Tsuchida, et al.
Hasegawa, *J. New Remedies & Clinics* (*Shinyaku to Rinsho*), 1999, vol. 48, No. 1, pp. 113-115, tables 1, 2.
Aoyama, *J. Hokkaido For Prod. Res., Inst.* (*Rinsanshijoho*), 1995, vol. 9, No. 6, pp. 1-8, table 2.
Zhang Hang et al, *Jpn. J. Pharm.* 1998, vol. 76, No. Suppl. 1. pp. 164p, p-127.
Internet website—http://www.usnews.com/usnews/health/allergy/hayfever/hay.prevent.htm (1 page total), accessed Dec. 31, 2005.

* cited by examiner

*Primary Examiner*—Susan C Hoffman
(74) *Attorney, Agent, or Firm*—Sughrue Mion, PLLC

(57) ABSTRACT

The present invention provides a composition for treating and/or preventing pollinosis which comprises an extract from *Sasa albo-marginata* in an amount ranging from 1 to 10% by mass as expressed in terms of the solid content of the extract. The composition of the present invention comprises a *Sasa albo-marginata* extract in a concentration considerably higher than that conventionally used and accordingly, it shows a high effect of treating and/or preventing various symptoms associated with serious pollinosis, which has been quite difficult to treat and/or prevent with the conventional anti-histamic agents or steroidal drugs, without accompanying any side-effect.

26 Claims, No Drawings

COMPOSITIONS FOR TREATING AND/OR PREVENTING POLLINOSIS

CROSS REFERENCE TO RELATED APPLICATIONS

This application is a continuation of application Ser. No. 10/949,367, filed Sep. 27, 2004 now abandoned, which is a continuation of International application PCT/JP03/03822, filed Mar. 27, 2003.

TECHNICAL FIELD

The present invention relates to a composition for treating and/or preventing pollinosis, which comprises an extract from *Sasa albo-marginata* (Bambooseae *Sasa*) as an effective component.

BACKGROUND ART

Recently, there have rapidly been increased the number of patients suffering from allergic symptoms (hereunder referred to as "pollinosis") accompanied by, for instance, conjunctivitis (itching and congestion of eyes), rhinitis (sneezing, snivel and nasal congestion) and bronchial asthma, which are caused due to the allergic hypersensitivity against pollens of, for instance, hinoki (white cedar), sugi (Japanese cedar) and ragweed (*Ambrosia artemisiifolia*), and dead bodies of, for instance, ticks or mites. In respect of pollinosis, a steroidal drug has been used for alleviating the related symptoms, but the symptoms have never been alleviated in a large number of patients even if such a steroidal drug is administered to these patients. Accordingly, there has been desired for the development of an effective means for treating and/or alleviating pollinosis.

DISCLOSURE OF THE INVENTION

It is thus an object of the present invention to provide a composition for treating and/or preventing pollinosis, which can ensure a high effect of treating and/or preventing pollinosis.

According to the present invention, there is provided a composition for treating and/or preventing pollinosis, which comprises an extract from *Sasa albo-marginata* (Bambooseae *Sasa*) in an amount ranging from 1 to 10% by mass as expressed in terms of the solid content of the extract.

The term "pollinosis" as used herein means the allergic symptoms (pollinosis in a broad sense), which are caused due to the allergic hypersensitivity against pollens of, for instance, hinoki (white cedar), sugi (Japanese cedar) and ragweed (*Ambrosia artemisiifolia*), and dead bodies of, for instance, ticks or mites and which are accompanied by, for instance, conjunctivitis (itching and congestion of eyes), rhinitis (sneezing, snivel and nasal congestion) and bronchial asthma, and more specifically, the term means the allergosis (pollinosis in a narrow sense), which are caused due to the allergic hypersensitivity against pollens and accompanied by, for instance, conjunctivitis (itching and congestion of eyes), rhinitis (sneezing, snivel and nasal congestion) and bronchial asthma.

BEST MODE FOR CARRYING OUT THE INVENTION

The present invention relates to a composition for treating and/or preventing pollinosis, which comprises an extract from *Sasa albo-marginata* in an amount ranging from 1 to 10% by mass, preferably 2 to 8% by mass and more preferably 3 to 6% by mass, as expressed in terms of the solid content of the extract. In this respect, if the content of the extract from *Sasa albo-marginata* is less than 1% by mass, the resulting composition is insufficient in the intended effect of treating and/or preventing the pollinosis, while if the content thereof exceeds 10% by mass, the composition would be too stimulative to the skin.

Conventionally, the *Sasa albo-marginata* extract has been prepared in the form of an extract having a solid content ranging from 0.5 to 10% by mass and has been used in a variety of applications. The extract having such a solid content has been used in such a manner that the content thereof in a final product in general ranges from about 1 to 10% by mass and therefore, the solid content of the *Sasa albo-marginata* extract in the final product in general ranges from about 0.05 to 0.8% by mass and at highest on the order of less than 1% by mass. The reason for this is, for instance, that the *Sasa albo-marginata* extract is relatively expensive, that the extract would show the anti-inflammatory effect and antibiotic action even in such a low concentration to some extent and that it would be unreasonable to increase the added amount of the effective component to a level of not less than 10% by mass. However, the product having such a low content of the extract is almost ineffective in the treatment and/or prevention of pollinosis.

The inventors of this invention have found that if the *Sasa albo-marginata* extract is present in a final product in a solid content ranging from 1 to 10% by mass, preferably 2 to 8% by mass and more preferably 3 to 6% by mass, the product shows a highly improved effect of treating and/or preventing pollinosis, which have never been recognized when using a conventional extract having a low solid content. Thus, the inventors of this invention have completed the present invention on the basis of these findings.

The *Sasa albo-marginata* extract per se has long been known, but there has never been tried any attempt to use an extract in such a high solid content. The reason for this has not yet been elucidated, but it has surprisingly been recognized that the use of such an extract in a concentration higher than that of the conventionally used one (not less than 10 times) would permit the significant improvement of the effect of treating and/or preventing pollinosis.

The *Sasa albo-marginata* used in the present invention, as a raw material for the extract thereof is not restricted to any specific one and any plant belonging to the genus *Sasa* may be used herein. Specific examples thereof include those specified below: Kumai *Sasa*; *Sasa albo-marginata* Makino et Shibata (Kuma *Sasa*); ground bamboo; Okuyama *Sasa*; Ezo-Miyama *Sasa*; *Sasa* Paniculata Makino et Shibata; Yahiko *Sasa*; Oba *Sasa*; Miyama *Sasa*; Sendai *Sasa*; Yukawa *Sasa*; Aboi *Sasa*; and Onuka *Sasa*. Among these, specific examples of commercially available ones include Kumai *Sasa* and Kuma *Sasa* (Chugoku *Sasa* and Hida *Sasa*). For instance, preferably used herein are extracts derived from, for instance, Kumai *Sasa* and/or Kuma *Sasa* collected in, for instance, TESHIO Mountains in Hokkaido during the term extending from July to October.

The *Sasa albo-marginata* extract used in the present invention is preferably one prepared by extracting raw leaves or dried leaves of *Sasa albo-marginata*, preferably dried leaves thereof with water maintained at a temperature ranging from 100 to 180° C. at ordinary pressure or while applying a pressure.

The extraction method is not restricted to any particular one, but usable herein includes, for instance, that disclosed in Japanese Patent No. 3,212,278 (Japanese Un-Examined Patent Publication Hei 11-196818). More specifically, leaves of *Sasa albo-marginata* are extracted at a temperature ranging from 100 to 180° C. for 5 to 30 minutes using a pressurized hot water extraction device, the resulting extract is separated into a moisture-containing solid content (moisture content: 40 to 70%) in a moisture separator, thereafter the moisture-containing solid content is treated at a temperature ranging from 100 to 200° C. for 5 to 60 minutes in a saturated vapor-heating device, the solid content thus treated is again treated at 100 to 180° C. for 5 to 30 minutes using a pressurized hot water extraction device and the extracts obtained in the first and second extraction steps are combined prior to practical use. Alternatively, it is also possible to use an extract obtained by extracting dried leaves of *Sasa albo-marginata* with, for instance, water heated to 60 to 100° C. for 30 minutes to 12 hours.

There has been known "AHSS" available from CHLORO-LAND.MOSHIRI CO., LTD as an example of commercially available one having a content of the *Sasa albo-marginata* extract of 50% by mass as expressed in terms of the solid content of the extract.

The *Sasa albo-marginata* extract thus obtained contains sulfur-containing components and the content thereof as expressed in terms of the amount of sulfur ranges from about 4 to 10 mg and usually about 6 to 9 mg per one gram of the solid content of the *Sasa albo-marginata* extract. Principal constituents of the sulfur-containing components are considered to be sulfur-containing amino acids.

The composition for treating and/or preventing pollinosis according to the present invention comprises such sulfur-containing components derived from the *Sasa albo-marginata* extract in an amount preferably ranging from 4 to 500 mg, more preferably 8 to 250 mg and most preferably 16 to 150 mg per 100 g of the composition, as expressed in terms of the amount of sulfur.

Moreover, the solid content of the *Sasa albo-marginata* extract contains tannin and the content thereof in the solid contents is in the order of about 5 to 15% by mass based on the mass of the solid contents present in the extract.

It is desirable that the composition for treating and/or preventing pollinosis according to the present invention comprise the tannin derived from the *Sasa albo-marginata* extract in an amount preferably ranging from 0.05 to 7.5% by mass and more preferably 0.1 to 6% by mass as expressed in terms of the concentration of the solid contents thereof.

The composition for treating and/or preventing pollinosis according to the present invention may comprise only the *Sasa albo-marginata* extract as an effective component or the simultaneous use of a reasonable amount of an organic acid would permit the further improvement of the resulting composition in its effect of treating and/or preventing pollinosis. Examples of such organic acids include malic acid, citric acid, lactic acid, oxalic acid, malonic acid, succinic acid, fumaric acid, acetic acid, benzoic acid, phenyl-acetic acid, salicylic acid and phenols.

The amount of such an organic acid used in the composition for treating and/or preventing pollinosis according to the present invention preferably ranges from 0.01 to 5% by mass, more preferably 0.02 to 3% by mass and most preferably 0.05 to 1.5% by mass based on the total mass of the composition.

In the preparation of the composition for treating and/or preventing pollinosis according to the present invention, there may be used, for instance, a basic component such as an oily component, a moisture retentive agent and/or a preservative (or an antiseptic), which are commonly used in pharmaceutical compositions, cosmetics and compositions applied to the skin, in addition to a desired amount of the foregoing *Sasa albo-marginata* extract.

The origins of the water used in the composition are not restricted to particular ones and examples thereof include tap water, natural water and purified water, but preferably used herein is highly purified water such as ion-exchange water.

Examples of oily components usable herein are oils derived from animals such as squalane, tallow, lard, horse fat, lanolin and beeswax; oils derived from vegetables such as olive oil, grape seed oil, palm oil, jojoba oil and germ oil (such as rice germ oil); and synthetic or semi-synthetic oils such as liquid paraffin, higher fatty acid esters (such as octyl palmitate, isopropyl palmitate and octyl dodecyl myristate) and silicone oil.

The oily components are used in appropriate combinations depending on the performance requirement, for instance, an ability of protecting the skin, an effect of imparting emollient (or an effect of preventing drying of the skin and imparting softness and resilience to the skin through the coverage of the skin surface with a thin film) and an ability of imparting refreshed feeling to the skin. In one of preferred examples of such combinations, the oily component comprises squalane, olive oil and octyl dodecyl myristate.

The composition comprises a solid oil component such as stearic acid, stearyl alcohol, behenic acid, cetanol and vaseline to control the hardness and flowability of the composition and the composition preferably comprises stearic acid and cetanol in combination.

When preparing the composition for treating and/or preventing pollinosis according to the present invention in the form of a cream composition, a creaming agent is used to convert the mixture of the *Sasa albo-marginata* extract, water and an oily component into a cream. Such a creaming agent is not restricted to any particular one, but glycerin monostearate and a self-emulsifiable glycerin monostearate (a product obtained by incorporating an emulsifying agent into glycerin monostearate) are in general used in combination.

Moreover, the composition for treating and/or preventing pollinosis according to the present invention may, if necessary, contain other additives such as a stabilizer, a moisture retentive agent, a wound-healing agent, a preservative and/or a surfactant.

Examples of stabilizers are a combination of a carboxy vinyl polymer with potassium hydroxide, and polyethylene glycol distearate. In particular, polyethylene glycol sesquistearate (a 1:1 mixture of polyethylene glycol distearate and polyethylene glycol monostearate) (molecular weight of the polyethylene glycol ranging from 1000 to 20,000) is preferably used herein since it has high stability, it is never separated into water and oil and the hardness required when the composition is applied to the skin in the form of a cream composition can effectively be controlled.

Examples of moisture retentive agents usable herein are sodium salt of hyaluronic acid, collagen, aloe extract (in particular, aloe extract (2) derived from Aloe arborescens is preferred), urea, 1,3-butylene glycol, glycerin, trehalose, sorbitol, amino acids and sodium salt of pyrrolidone carboxylic acid.

Examples of wound-healing agents usable herein are allantoin, dipotassium glycyrrhizinate, glycyrrhiza extract and mugwort extract.

The preservative (or antiseptic) is used subsidiarily since the *Sasa albo-marginata* extract has an antibiotic effect by nature. Examples of such preservatives are sodium benzoate, lower alkyl esters of p-hydroxy benzoic acid (for instance, so-called paraben such as methyl, ethyl, propyl or butyl ester), sodium propionate, mixed fatty acid esters (a mixture of capric acid glyceryl, lauric acid polyglyceryl-2 and lauric acid polyglyceryl-10), phenoxytal, and light-sensitive substance No. 201 (yellow dye), with paraben and mixed fatty acid esters being preferably used herein.

Examples of surfactants are sodium N-acyl-L-glutamate and polyoxyethylene sorbitan monostearate.

In addition, the composition may, if required, comprise aroma components such as orange oil, lemon oil, bitter orange peel oil and perfumes.

Water and, if necessary, an organic acid are added to the foregoing components to make the total amount of the resulting composition 100% by mass.

The following Table 1 shows preferred amounts (% by mass) of the foregoing ingredients required for preparing the composition for treating and/or preventing pollinosis according to the invention in the form of a cream composition. The amount of each component other than water corresponds to the mass thereof free of any moisture.

TABLE 1

| Component | Preferred range | More preferred range | Most preferred range |
|---|---|---|---|
| Sasa albo-marginata extract | 1 to 10 | 2 to 8 | 3 to 6 |
| Liquid oily component | 6 to 30 | 2 to 20 | 5 to 15 |
| Solid oily component | 2 to 35 | 3 to 25 | 5 to 15 |
| Creaming agent | 1 to 6 | 1.5 to 4 | 1.6 to 3 |
| Stabilizer | 0 to 2 | 0 to 1.5 | 0 to 1 |
| Moisture retentive agent | 0 to 10 | 0.05 to 5 | 0.1 to 5 |
| Wound-healing agent | 0 to 2 | 0.05 to 1 | 0.1 to 0.5 |
| Aroma component | 0 to 5 | 0 to 3 | 0 to 1 |
| Organic acid | 0.01 to 5 | 0.1 to 3 | 0.5 to 1.5 |
| Water | Balance | Balance | Balance |

The foregoing components are introduced into a heating-mixing kettle equipped with a stirring blade and preferably an emulsification apparatus and they are then admixed together at 70 to 90° C. for one to two hours to form a composition for treating and/or preventing pollinosis according to the invention.

The composition for treating and/or preventing pollinosis according to the invention may be used in various dosage forms other than a cream composition such as an ointment, a liquid, a jelly, an eye drop and other forms, with a cream composition being preferred because it can easily be used and shows a considerable effect.

Alternatively, the composition of the present invention may likewise be used in the form of a mask obtained by impregnating a substrate such as absorbent gauze with the Sasa albo-marginata extract at a high temperature of preferably not less than 80° C. in an amount ranging from 1 to 10% by mass as expressed in terms of the solid content of the extract and then drying the impregnated substrate and the resulting mask is also effectively used for treating and/or preventing pollinosis.

It is sufficient to apply the composition of the present invention to the affected part, after cleaning the same, in an appropriate amount thereof, for instance, 0.1 to 1 g per 100 cm$^2$ of the skin in case of a cream composition over 1 to 5 times, usually 1 to 3 times a day.

In case of, for instance, the itching of eyes, it is likewise sufficient to apply a cream composition to the eyelids, in particular, the periphery thereof and/or the lower eyelid of a patient. It is also possible to apply an eye drop to the eyes of a patient. Such an eye drop may desirably comprise 2 to 8% by mass and preferably 2 to 3% by mass of the Sasa albo-marginata extract as expressed in terms of the solid content thereof. The amount and number of application of the composition or the number of dropping thereof in the eyes may appropriately be changed while taking into consideration, for instance, the extent of pollinosis. When applying the composition for treating and/or preventing pollinosis according to the invention to the affected part, the typical symptoms of pollinosis (such as itching and congestion of eyes, sneezing, snivel and nasal congestion) would rapidly be alleviated or eliminated within the term generally ranging from about 5 to 10 minutes.

The composition of the present invention comprises 1 to 10% by mass of the Sasa albo-marginata extract as expressed in terms of the solid content and accordingly, the composition would show a considerable effect of improving various symptoms associated with the pollinosis.

The following are preferred embodiments of the composition for treating and/or preventing pollinosis according to the present invention.

1. A composition for treating and/or preventing pollinosis, which comprises the Sasa albo-marginata extract (1 to 10% by mass as expressed in terms of the solid content), water, an oily component and a creaming agent.
2. The composition according to the foregoing item 1 in which the oily component is at least one member selected from the group consisting of animal oil, vegetable oil, synthetic oil and semi-synthetic oil.
3. The composition according to the foregoing item 1 in which the oily component is at least one member selected from the group consisting of squalane, tallow, lard, horse fat, lanolin, beeswax, olive oil, grape seed oil, palm oil, jojoba oil, germ oil, liquid paraffin, octyl palmitate, isopropyl palmitate, octyl dodecyl myristate, silicone oil, stearic acid, stearyl alcohol, behenic acid, cetanol and vaseline.
4. The composition according to any one of the foregoing items 1 to 3 in which the creaming agent is a combination of glycerin monostearate with self-emulsifiable glycerin monostearate.
5. The composition according to any one of the foregoing items 1 to 4 which further comprises at least one component selected from the group consisting of a stabilizer, a moisture retentive agent, a wound-healing agent, a preservative and a surfactant.
6. The composition according to the foregoing item 5 in which the stabilizer is at least one member selected from the group consisting of a combination of a carboxy vinyl polymer with potassium hydroxide, and polyethylene glycol distearate.
7. The composition according to the foregoing item 5 in which the moisture retentive agent is at least one member selected from the group consisting of sodium salt of hyaluronic acid, collagen, aloe extract, urea, 1,3-butylene glycol, glycerin, trehalose, sorbitol, amino acids and sodium salt of pyrrolidone carboxylic acid.
8. The composition according to the foregoing item 5 in which the wound-healing agent is at least one member selected from the group consisting of allantoin, dipotassium glycyrrhizinate, glycyrrhiza extract and mugwort extract.
9. The composition according to the foregoing item 5 in which the preservative is at least one member selected from the group consisting of sodium benzoate, lower alkyl esters of p-hydroxy benzoic acid, sodium propionate, mixed fatty acid esters, phenoxytal, and yellow dye.

10. The composition according to the foregoing item 5 which further comprises at least one member selected from the group consisting of orange oil, lemon oil, bitter orange peel oil and perfumes.
11. The composition according to the foregoing item 10, which comprises a *Sasa albo-marginata* extract, water, an oily component, a creaming agent, a stabilizer, a moisture retentive agent, a wound-healing-promoting agent, a preservative and a surfactant, wherein the oily component is at least one member selected from the group consisting of squalane, tallow, lard, horse fat, lanolin, beeswax, olive oil, grape seed oil, palm oil, jojoba oil, germ oil, liquid paraffin, octyl palmitate, isopropyl palmitate, octyl dodecyl myristate, silicone oil, stearic acid, stearyl alcohol, behenic acid, cetanol and vaseline; the creaming agent is a combination of glycerin monostearate with self-emulsifiable glycerin monostearate; the stabilizer is at least one member selected from the group consisting of a combination of a carboxy vinyl polymer with potassium hydroxide and polyethylene glycol distearate; the moisture retentive agent is at least one member selected from the group consisting of sodium salt of hyaluronic acid, collagen, aloe extract, urea, 1,3-butylene glycol, glycerin, trehalose, sorbitol, amino acids and sodium salt of pyrrolidone carboxylic acid; the wound-healing agent is at least one member selected from the group consisting of allantoin, dipotassium glycyrrhizinate, glycyrrhiza extract and mugwort extract; the preservative is at least one member selected from the group consisting of sodium benzoate, lower alkyl esters of p-hydroxy benzoic acid, sodium propionate, mixed fatty acid esters, phenoxytal, and yellow dye; and the surfactant is sodium N-acyl-L-glutamate.
12. The composition as set forth in the foregoing item 11 which further comprises at least one member selected from the group consisting of orange oil, lemon oil, bitter orange peel oil and perfumes.
13. The composition as set forth in the foregoing item 1 which comprises a *Sasa albo-marginata* extract, water, squalane, olive oil, glycerin monostearate, self-emulsifiable glycerin monostearate, a carboxy vinyl polymer, potassium hydroxide, urea, 1,3-butylene glycol, allantoin, a lower alkyl ester of p-hydroxy benzoic acid, stearic acid, sodium N-acyl-L-glutamate and lemon oil.
14. The composition as set forth in the foregoing item 1 which comprises a *Sasa albo-marginata* extract, water, squalane, olive oil, octyl dodecyl myristate, cetanol, glycerin monostearate, self-emulsifiable glycerin monostearate, a carboxy vinyl polymer, potassium hydroxide, urea, 1,3-butylene glycol, allantoin, a mixed fatty acid ester, stearic acid, sodium N-acyl-L-glutamate and orange oil.
15. The composition as set forth in any one of the foregoing items 1 to 14 which comprises polyethylene glycol sesquistearate.
16. A composition for treating and/or preventing pollinosis which comprises an aqueous solution containing a *Sasa albo-marginata* extract (1 to 10% by mass as expressed in terms of the solid content).
17. The composition of the foregoing item 16 in which it is in the form of an eye drop or a mouthwash.

The present invention will hereunder be described in more detail with reference to the following Reference Examples, working Examples and Test Examples.

REFERENCE EXAMPLE 1

Preparation of *Sasa albo-marginata* Extract

Dried leaves of the *Sasa albo-marginata* collected in TESHIO Mountains in Hokkaido Japan in September were introduced into a pressurized hot water extraction tank, treated at 125° C. for 10 minutes in the tank, the hot water was cooled down to about 80° C. by the action of a cooling water and then the resulting extract was separated from the moisture-containing solid content using a screw-press in such a manner that the moisture content of the latter was controlled to a level of about 50% by mass. Then the solid contents having a moisture content of about 50% by mass were introduced into an autoclave and heat-treated under pressure at 180° C. for 10 minutes using saturated steam. The moisture-containing solid contents thus treated were again introduced into a pressurized hot water-extraction tank and treated at 110° C. for 5 minutes to thus obtain an extract. The first and second extracts were combined together, filtered through a diatomaceous earth layer, the resulting filtrate was concentrated under reduced pressure till the solid content thereof was increased to 50% by mass and the concentrate thus prepared was subjected to a fluidized sterilization treatment at a temperature ranging from 110 to 130° C. to give a *Sasa albo-marginata* extract.

The *Sasa albo-marginata* extract was inspected for the sulfur content and it was found to be 3850 μm/ml (7.7 mg per one gram of the solid content).

REFERENCE EXAMPLE 2

The commercially available *Sasa albo-marginata* extract (the extract derived from Bambuseae *Sasa*; available from HOUOUDOU Co., Ltd.) was inspected for the components thereof and as a result, the extract included the following components: Water: 59.5% by mass; Proteins: 8.6% by mass; Lipid: 0.6% by mass; Minerals: 9.0% by mass; Carbohydrates: 19.8% by mass; and Tannin: 2.5% by mass.

EXAMPLES 1 TO 4

The components listed in the following Table 2 were admixed together in amounts (% by mass) likewise specified in Table 2, introduced into a heating and mixing kettle equipped with a stirring blade and an emulsification apparatus and then mixed therein with stirring at 80° C. for 2 hours to thus give a cream composition for treating and/or preventing pollinosis according to the present invention. The added amounts of a *Sasa albo-marginata* extract having a solid content of 8% by mass (a product obtained by diluting the *Sasa albo-marginata* extract having a solid content of 50% by mass and prepared in Reference Example 1) were 12.5, 25, 37.5 and 75% by mass respectively (therefore, the contents of the extract as expressed in terms of the solid content thereof were 1, 2, 3 and 6% by mass; and sulfur contents of these samples were 7.7 mg, 15.4 mg, 23.1 mg and 46.2 mg per 100 g of the composition, respectively).

TABLE 2

| Component | Amount (% by mass) |
| --- | --- |
| Squalane | 5.0 |
| Olive oil | 6.0 |
| Lemon oil | 1.0 |
| Stearic acid | 4.0 |
| Glycerin monostearate | 0.8 |
| Carboxy vinyl polymer (CARBOPOL 940) | 0.2 |
| Glycerin monostearate (self-emulsifiable type) | 1.0 |
| Sodium N-acyl-L-glutamate | 0.2 |
| 1,3-Butylene glycol | 1.0 |
| Urea | 10.0 |
| Allantoin | 0.1 |
| Methyl p-oxy-benzoate | 0.1 |
| Propyl p-oxy-benzoate | 0.1 |
| Sasa albo-marginata extract (solid content 8% by mass) | Desired amount |
| Potassium hydroxide | 0.02 |
| Ion-exchange water | Balance |

EXAMPLE 5

The same procedures used in Examples 1 to 4 were repeated using the components shown in the following Table 3 in the amounts likewise specified in Table 3 to thus give each corresponding cream composition for treating and/or preventing pollinosis according to the present invention.

TABLE 3

| Component | Amount (% by mass) |
| --- | --- |
| Squalane | 1.0 |
| Olive oil | 4.0 |
| Orange oil | 1.0 |
| Octyl dodecyl myristate | 5.0 |
| Stearic acid | 4.0 |
| Cetanol | 2.0 |
| Polyethylene glycol di-stearate | 0.5 |
| Glycerin monostearate | 1.0 |
| Carboxy vinyl polymer (CARBOPOL 940) | 0.2 |
| Glycerin monostearate (self-emulsifiable type) | 1.4 |
| Sodium N-acyl-L-glutamate | 0.2 |
| 1,3-Butylene glycol | 1.0 |
| Urea | 3.0 |
| Allantoin | 0.1 |
| Mixed fatty acid ester (NIKOGUARD DL) | 0.5 |
| Sasa albo-marginata extract (solid content: 8% by mass) | 75.0 |
| Potassium hydroxide | 0.05 |
| Ion-exchange water (ad. 100 ml) | 0.05 |

The resulting composition was found to have a sulfur content of 46.2 mg per 100 g thereof.

EXAMPLE 6

The components listed in the following Table 4 were admixed together in amounts (% by mass) likewise specified in Table 4, introduced into a heating and mixing kettle equipped with a stirring blade and an emulsification apparatus and then mixed therein with stirring at 80° C. for 2 hours to thus give a cream composition for treating and/or preventing pollinosis according to the present invention.

TABLE 4

| Component | Amount (% by mass) |
| --- | --- |
| Liquid paraffin | 10.0 |
| Squalane | 1.0 |
| Olive oil | 1.0 |
| Orange oil | 1.0 |
| Octyl dodecyl myristate | 6.0 |
| 1,2-Pentanediol | 0.5 |
| Phenoxy-ethanol | 0.5 |
| Cetanol | 1.5 |
| Stearic acid | 4.0 |
| Glycerin monostearate | 2.0 |
| Glycerin monostearate (self-emulsifiable type) | 2.5 |
| Polyethylene glycol di-stearate | 0.5 |
| Carboxy vinyl polymer | 0.3 |
| Sodium N-acyl-L-glutamate | 0.2 |
| 1,3-Butylene glycol | 1.0 |
| Ethanol | 3.0 |
| Tri-methyl glycine | 0.5 |
| Sodium hyaluronate | 1.0 |
| Sasa albo-marginata extract (solid content: 50% by mass) | 12.0 |
| Purified water | 51.5 |

The pH value of the resulting cream was found to be 6.00.

EXAMPLE 7

The components listed in the following Table 5 were admixed together in amounts (% by mass) likewise specified in Table 5, introduced into a heating and mixing kettle equipped with a stirring blade and an emulsification apparatus and then mixed therein with stirring at 80° C. for 2 hours to thus give a cream composition for treating and/or preventing pollinosis according to the present invention.

TABLE 5

| Component | Amount (% by mass) |
| --- | --- |
| Olive oil | 3.0 |
| Squalane | 1.0 |
| Liquid paraffin | 3.0 |
| Cetanol | 1.3 |
| Glycerin monostearate | 2.0 |
| Glycerin monostearate (self-emulsifiable type) | 5.0 |
| Polyoxyethylene (20) stearyl ether | 1.0 |
| Polyoxyethylene (20) cetyl ether | 1.0 |
| Polyoxyethylene (140) monostearate | 1.0 |
| Bentonite | 0.5 |
| Xanthane gum | 0.2 |
| Glucono-δ-lactone | 4.0 |
| dl-Malic acid | 1.0 |
| Triethanolamine | 3.3 |
| 1,2-Pentanediol | 0.5 |
| Phenoxy-ethanol | 0.5 |
| 1,3-Butylene glycol | 2.0 |
| Sasa albo-marginata extract (solid content: 50% by mass) | 12.0 |
| Purified water | 57.7 |

The pH value of the resulting cream was found to be 4.68.

EXAMPLES 8 TO 10

The same procedures used in Example 7 were repeated except that dl-malic acid was not added, that the amount of the *Sasa albo-marginata* extract (solid content: 50% by mass) used was changed to 16, 20 or 30% by mass and that the amount of the purified water was correspondingly controlled to thus give each corresponding cream for treating and/or preventing pollinosis according to the present invention, which had a content of the *Sasa albo-marginata* extract (amount of the solid content thereof) was 8, 10 or 15% by mass.

EXAMPLES 11 TO 13

The same procedures used in Example 7 were repeated except that the amount of the *Sasa albo-marginata* extract (solid content: 50% by mass) used was changed to 16, 20 or 30% by mass and that the amount of the purified water was correspondingly controlled to thus give each corresponding cream for treating and/or preventing pollinosis according to the present invention, which had a content of the *Sasa albo-marginata* extract (amount of the solid content thereof) was 8, 10 or 15% by mass.

Test Example 1

Effect of Alleviating the Symptoms of Patients Suffering from Pollinosis

When applying, to patients suffering from pollinosis, the cream composition (having a content of the solid contents of the *Sasa albo-marginata* extract equal to 2% by mass) for treating and/or preventing pollinosis which was prepared in Example 2, there were observed the results listed in the following Table 6. Table 6 also shows the symptoms of the patients (affected parts, extent of the symptoms), the site to which the composition was applied and the extent of effects achieve. The extent of the patients' symptom was evaluated according to the following three stage criteria: A: serious; B: medium; and C: mild.

TABLE 6

| Patient No.; Sex (age) | Eye | Nose | Throat | Others | Effects |
|---|---|---|---|---|---|
| 1; male (43) | — | B | — | — | Quick acting |
| 2; male (43) | A | A | — | — | Quick acting |
| 3; female (28) | A | A | — | — | Sparingly effective |
| 4; male (29) | A | A | — | — | Effective |
| 5; male (39) | C | — | — | — | Effective |
| 6; female (33) | A | A | — | — | Effective only for 2 to 3 hours |
| 7; male (31) | A | A | — | — | Effective |
| 8; male (48) | A | A | — | — | Effective |
| 9; male (51) | A | A | — | — | Effective |
| 10; male (58) | B | B | — | — | Effective |
| 11; female (12) | B | B | — | — | Effective |
| 12; male (38) | — | A | — | — | Effective |
| 13; female (19) | A | A | — | — | Effective |
| 14; male (42) | B | B | — | — | Slightly effective |
| 15; male (51) | A | A | — | — | Effective |
| 16; male (29) | A | A | — | — | Effective |
| 17; male (48) | A | A | — | — | Slightly effective |
| 18; female (45) | A | A | — | — | Effective |
| 19; male (28) | A | A | — | — | Effective |
| 20; male (59) | — | B | — | — | Effective |
| 21; female (55) | A | A | — | — | Effective |
| 22; male (60) | A | A | — | — | Effective |
| 23; male (38) | B | B | — | — | Effective |
| 24; female (29) | — | C | — | — | Effective |
| 25; female (60) | — | B | — | — | Effective |
| 26; female (45) | A | A | — | — | Effective |
| 27; male (20) | — | B | — | — | Effective |
| 28; female (62) | A | A | — | — | Effective (simultaneously using an anti-histamic agent) |
| 29; female (45) | A | A | — | — | Significantly effective |
| 30; female (45) | — | B | — | — | Effective (simultaneously using an anti-histamic agent) |
| 31; male (35) | — | B | — | — | Effective |
| 32; male (55) | — | A | — | — | Effective (simultaneously using an anti-histamic agent) |
| 33; male (39) | — | B | — | — | Effective |
| 34; female (31) | — | B | — | — | Effective |
| 35; female (46) | A | A | B* | — | Effective (simultaneously using an anti-histamic agent) |
| 36; male (50) | — | B | — | — | Effective |
| 37; male (47) | — | B | — | — | Effective |
| 38; female (22) | — | B | — | — | Effective |
| 39; female (64) | — | A | — | — | Significantly effective |
| 40; female (27) | — | B | — | — | Quick acting |
| 41; male (20) | — | A | — | — | Effective |
| 42; male (42) | — | A | — | — | Effective |

*The patient rinsed out her mouth with an aqueous solution containing the Sasa albo-marginata extract in an amount of 2% by mass as expressed in terms of the solid content.

The data listed in Table 6 clearly indicate that the composition of the present invention has an effect of alleviating the symptoms of a large number of patients suffering from pollinosis. The composition of the invention may be used in combination with an anti-histamic agent and in such case, the composition would permit the reduction of the amount of the anti-histamic agent to be used.

INDUSTRIAL APPLICABILITY

The composition for treating and/or preventing pollinosis according to the present invention, which comprises a *Sasa albo-marginata* extract in an amount ranging from 1 to 10% by mass as expressed in terms of the solid content, can show, in a clinical level, a quite significant effect of treating and/or preventing pollinosis for which there has not yet been proposed any effective pollinosis-treating and/or preventing composition and it is excellent in that it has no side-effect. More specifically, the composition of the present invention shows a quite significant effect of treating and/or preventing the allergic symptoms (pollinosis in a broad sense), which are caused due to the allergic hypersensitivity against pollens of, for instance, hinoki (white cedar), sugi (Japanese cedar) and ragweed (*Ambrosia artemisiifolia*), and dead bodies of, for instance, ticks or mites and which are accompanied by, for instance, conjunctivitis (itching and congestion of eyes), rhinitis (sneezing, snivel and nasal congestion) and bronchial asthma, and in particular, the allergosis (pollinosis in a narrow sense), which are caused due to the allergic hypersensitivity against pollens and accompanied by, for instance, conjunctivitis (itching and congestion of eyes), rhinitis (sneezing, snivel and nasal congestion) and bronchial asthma, without any side-effect.

What is claimed is:
1. A method for treating pollinosis in a patient in need thereof, comprising
    administering a composition comprising an extract of *Sasa albo-marginata* to the patient in need thereof, in an amount sufficient to treat the pollinosis, wherein the composition comprises from 1 to 10% by mass of the *Sasa albo-marginata* extract, as expressed in terms of the solid content of the extract, wherein the composition comprises components comprising sulfur, wherein the components are obtained from the *Sasa albo-marginata* extract, and wherein the components are present in an amount ranging from 4 to 100 mg per 100 g of the composition as expressed in terms of the amount of sulfur.

2. The method of claim 1, wherein the composition is in the form of a cream.

3. The method of claim 1, wherein the composition further comprises an organic acid.

4. The method of claim 3, wherein the organic acid is at least one acid selected from the group consisting of malic acid, citric acid, lactic acid, oxalic acid, malonic acid, succinic acid, fumaric acid, acetic acid, benzoic acid, phenylacetic acid, salicylic acid, and a phenol.

5. The method of claim 4, wherein the at least one acid comprises malic acid.

6. The method of claim 5, wherein the amount of malic acid in the composition ranges from 0.01 to 5% by mass based on the total mass of the composition.

7. The method of claim 4, wherein the amount of the organic acid in the composition ranges from 0.01 to 5% by mass, based on the total mass of the composition.

8. The method of claim 1, wherein the composition further comprises a tannin, and wherein the tannin is obtained from *Sasa albo-marginata*.

9. The method of claim 1, wherein the composition comprises from 2 to 8% by mass of the *Sasa albo-marginata* extract, as expressed in terms of the solid content of the extract.

10. The method of claim 9, wherein the composition is in the form of a cream.

11. The method of claim 9, wherein the composition further comprises an organic acid.

12. The method of claim 11, wherein the organic acid is at least one acid selected from the group consisting of malic acid, citric acid, lactic acid, oxalic acid, malonic acid, succinic acid, fumaric acid, acetic acid, benzoic acid, phenylacetic acid, salicylic acid, and a phenol.

13. The method of claim 12, wherein the at least one acid comprises malic acid.

14. The method of claim 13, wherein the amount of malic acid in the composition ranges from 0.01 to 5% by mass based on the total mass of the composition.

15. The method of claim 11, wherein the amount of the organic acid in the composition ranges from 0.01 to 5% by mass, based on the total mass of the composition.

16. The method of claim 9, wherein the composition further comprises a tannin, and wherein the tannin is obtained from *Sasa albo-marginata*.

17. A method for treating an allergic symptom caused by allergic hypersensitivity against a pollen or a dead body of a tick or a mite, in a patient in need thereof, comprising
administering a composition comprising an extract of *Sasa albo-marginata* to the patient in need thereof, in an amount sufficient to treat the allergic symptoms, wherein the composition comprises from 1 to 10% by mass of *Sasa albo-marginata* extract, as expressed in terms of the solid content of the extract, wherein the composition comprises components comprising sulfur, wherein the components are obtained from the *Sasa albo-marginata* extract, and wherein the components are present in an amount ranging from 4 to 100 mg per 100 g of the composition as expressed in terms of the amount of sulfur.

18. The method of claim 17, wherein the composition comprises from 2 to 8% by mass of the *Sasa albo-marginata* extract, as expressed in terms of the solid content of the extract.

19. The method of claim 17, wherein the composition is in the form of a cream.

20. The method of claim 17, wherein the composition further comprises an organic acid.

21. The method of claim 20, wherein the organic acid is at least one acid selected from the group consisting of malic acid, citric acid, lactic acid, oxalic acid, malonic acid, succinic acid, fumaric acid, acetic acid, benzoic acid, phenylacetic acid, salicylic acid, and a phenol.

22. The method of claim 21, wherein the at least one acid comprises malic acid.

23. The method of claim 22, wherein the amount of the malic acid in the composition ranges from 0.01 to 5% by mass, based on the total mass of the composition.

24. The method of claim 20, wherein the amount of the organic acid in the composition ranges from 0.01 to 5% by mass, based on the total mass of the composition.

25. The method of claim 17, wherein the allergic hypersensitivity comprises at least one disease selected from the group consisting of conjunctivitis, rhinitis, and bronchial asthma.

26. The method of claim 17, wherein the allergic symptom comprises at least one symptom selected from the group consisting of itching of the eyes, congestion of the eyes, sneezing, sniveling, nasal congestion, and bronchial constriction.

* * * * *